(12) United States Patent
Stark

(10) Patent No.: US 7,351,374 B2
(45) Date of Patent: Apr. 1, 2008

(54) SURFACE PLASMON ENHANCED ILLUMINATION APPARATUS HAVING NON-PERIODIC RESONANCE CONFIGURATIONS

(75) Inventor: Peter Randolph Hazard Stark, Andover, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 11/457,962

(22) Filed: Jul. 17, 2006

(65) Prior Publication Data

US 2007/0001125 A1 Jan. 4, 2007

Related U.S. Application Data

(63) Continuation-in-part of application No. 10/218,928, filed on Aug. 14, 2002, which is a continuation-in-part of application No. 09/981,280, filed on Oct. 16, 2001, now Pat. No. 6,818,907.

(60) Provisional application No. 60/699,454, filed on Jul. 15, 2005, provisional application No. 60/312,214, filed on Aug. 14, 2001, provisional application No. 60/293,153, filed on May 23, 2001, provisional application No. 60/240,886, filed on Oct. 17, 2000.

(51) Int. Cl.
*C12Q 1/68* (2006.01)
*G01N 21/00* (2006.01)
*G01N 15/06* (2006.01)
*G01N 33/00* (2006.01)
*G01N 33/48* (2006.01)

(52) U.S. Cl. .............. 422/50; 250/491.1; 250/492.1; 250/493.1; 422/55; 422/58; 422/68.1; 422/82.05; 422/82.08; 422/82.07; 422/82.09; 436/43; 436/63; 436/164; 436/172; 29/592; 29/592.1; 73/1.01; 73/1.02

(58) Field of Classification Search ............. 250/491.1, 250/492.1, 493.1; 422/50, 55, 58, 68.1, 82.05, 422/82.08, 82.07, 82.09; 436/43, 63, 164, 436/172; 29/592, 592.1; 73/1.01, 1.02
See application file for complete search history.

(56) References Cited

U.S. PATENT DOCUMENTS

5,973,316 A  10/1999  Ebbesen et al.
(Continued)

FOREIGN PATENT DOCUMENTS

| WO | WO 2003/019245 A2 | 3/2003 |
| WO | WO 2005/017570 A2 | 2/2005 |

OTHER PUBLICATIONS

Ebbesen, T.W., et al., "Extraordinary optical transmission through sub-wavelength hole arrays," *Nature*, vol. 391, pp. 667-669 (1998).
(Continued)

*Primary Examiner*—Brian Sines
(74) *Attorney, Agent, or Firm*—Wolf, Greenfield & Sacks, P.C.

(57) ABSTRACT

An apparatus configured to generate surface plasmon enhanced radiation comprises a metal film having first and second surfaces, and one or more resonance configurations formed in the metal film. An exemplary resonance configuration includes an aperture extending between the first and second surfaces of the metal film, and at least one feature that forms a non-periodic structure together with the aperture. The feature causes a variation in a dielectric function along the first surface of the metal film proximate to the aperture, and the aperture and the feature are configured so as to cooperatively facilitate a resonance condition for surface plasmon enhanced radiation generated by the apparatus, based on incident radiation that irradiates the first surface of the metal film. Exemplary features for a given resonance configuration include, but are not limited to, a single feature including one of another aperture, a protrusion that extends outwardly from the metal film, or a depression in the metal film, as well as one or more edges of the metal film.

42 Claims, 10 Drawing Sheets

U.S. PATENT DOCUMENTS

| | | |
|---|---|---|
| 6,052,238 A | 4/2000 | Ebbesen et al. |
| 6,236,033 B1 | 5/2001 | Ebbesen et al. |
| 6,285,020 B1 | 9/2001 | Kim et al. |
| 6,649,901 B2 | 11/2003 | Thio et al. |
| 6,818,907 B2 | 11/2004 | Stark |
| 6,834,027 B1 | 12/2004 | Sakaguchi et al. |
| 2002/0056816 A1 | 5/2002 | Randolph |
| 2003/0173501 A1 | 9/2003 | Tineke et al. |
| 2005/0094277 A1 | 5/2005 | Khusnatdinov Niyaz et al. |

OTHER PUBLICATIONS

Ghaemi, H.F., et al., "Surface plasmons enhance optical transmission through subwavelength holes," *Phys. Rev.*, vol. B 58, pp. 6779-6782 (1998).

Grupp, D.E., et al., "Crucial role of metal surface in enhance transmission through subwavelength apertures," *App. Phys. Lett.*, vol. 77, pp. 1569-1571 (2000).

Grupp, D.E., et al., "Beyond the Behte Limit: Tunable Enhanced Light Transmission Through a Single Sub-Wavelength Aperture," *Adv. Mater.*, vol. 11, pp. 860-862 (1999).

Jung, L.S., et al., "Quantitative Interpretation of the Response of Surface Plasmon Resonance Sensors to Adsorbed Films," *Langmuir*, vol. 14, No. 19, pp. 5636-5648 (1998).

Kim, T.J., et al., "Control of optical transmission through metals perforated with subwavelength hole arrays," *Opt. Lett.*, vol. 24, pp. 256-258 (1999).

Lezec, H.J., et al., "Beaming light from a subwavelength aperture," *Science*, vol. 297, pp. 820-822 (2002).

Raether, H., Surface Plasmons on Smooth and Rough Surfaces and on Gratings (Springer-Verlag, 1988).

Sandoz, P., et al., "Multi-aperture optical head for parallel scanning near field optical microscopy,".

Sonnichsen, C., et al., "Launching surface plasmons into nanoholes in metal films," *App. Phys. Lett.*, vol. 76, pp. 140-142 (2000).

Strelniker, Y.M., et al., "Optical transmission through metal films with a wubwavelength hole array in the presence of a magnetic field," *Phys. Rev.*, vol. B 59, pp. 12763-12766 (1999).

Thio, T., et al., "Enhanced light transmission through a single subwavelength aperture," *Optics Letters*, vol. 26, No. 24, pp. 1972-1974 (2001).

Thio T., et al., "Strongly enhanced optical transmission through subwavelength holes in metal films", Physica B. Condensed Matter, vol. 279, 2000, pp. 90-93.

SURFACE PLASMON ENHANCED ILLUMINATION APPARATUS HAVING NON-PERIODIC RESONANCE CONFIGURATIONS

CROSS-REFERENCE TO RELATED APPLICATIONS

This application claims the benefit, under 35 U.S.C. §119(e), of U.S. Provisional Application Ser. No. 60/699,454, filed Jul. 15, 2005, and entitled "Enhanced Surface Plasmon Light Transmission Through a Single Aperture Spaced From a Single Additional Surface Discontinuity or Defined Through a Smooth Resonant Surface."

This application also claims the benefit, under 35 U.S.C. §120, as a continuation-in-part (CIP) of U.S. Nonprovisional application Ser. No. 10/218,928, filed Aug. 14, 2002, entitled "Surface Plasmon Enhanced Illumination System."

Ser. No. 10/218,928 claims the benefit, under 35 U.S.C. §120, as a continuation-in-part (CIP) of U.S. Nonprovisional application Ser. No. 09/981,280, filed on Oct. 16, 2001, entitled "Surface Plasmon Enhanced Illumination System," now U.S. Pat. No. 6,818,907.

Ser. No. 09/981,280 claims the benefit, under 35 U.S.C. §119(e), of the following U.S. Provisional Applications:

Ser. No. 60/312,214, filed Aug. 14, 2001, entitled "Multiple Aperture Near Field Illumination System;"

Ser. No. 60/293,153, filed May 23, 2001, entitled "Surface Plasmon Enhanced Illumination System;" and Ser. No. 60/240,886, filed Oct. 17, 2000, entitled "Multiple Aperture Near Field Illumination System."

Each of the foregoing applications hereby is incorporated herein by reference.

FIELD OF THE DISCLOSURE

The present disclosure relates to methods and apparatus in which target areas are illuminated with one or more spots or lines of light having very small dimensions.

BACKGROUND

Typical optical microscopy (far-field light microscopy) cannot resolve distances less than the Rayleigh limit. The Rayleigh criterion states that two images are regarded as just resolved when the principal maximum (of the Fraunhofer diffraction pattern) of one coincides with the first minimum of the other [see Born, M. and Wolf, E. Principles of Optics. Cambridge University Press 6.sup.th ed. p. 415 (1980)]. For a circular aperture, this occurs at $$w = 0.61 \frac{\lambda}{NA}.$$

For example, the wavelength ($\lambda$) at the peak emission of a green fluorescent protein (EGFP) is 508 nm. Hence, for a very high numerical aperture (NA) of the objective, NA of 1.4, the minimum separation (w) that can be resolved in a GFP labeled sample is 221 nm. Currently, there are several possible methods for achieving resolution of spatial locations of proteins below the Rayleigh limit. They include: Confocal Microscopy, Fluorescence Resonance Energy Transfer (FRET), Atomic Force Microscopy (AFM), Near-Field Scanning Optical Microscopy (NSOM), Harmonic Excitation Light-Microscopy (HELM), Stimulated Emission Depletion Microscopy (STED-Microscopy) and Electron Microscope Immunocytochemistry.

Confocal Microscopy is a technique in which a very small aperture(s) is/are placed in the optical path to eliminate any unfocused light. This allows for a substantial increase in signal to noise ratio over conventional light microscopy. Also, it is possible to reduce the width of the central maximum of the Fraunhoffer pattern using a small slit or aperture. This, in turn allows a substantially enhanced resolution of 1.4 times better than the Rayleigh limit. Therefore, with this method, using the above protein as an example, a spatial resolution of 156 nm is achieved.

Typical confocal microscopy is not without disadvantages. By increasing the signal to noise ratio by decreasing the aperture size, the total signal level decreases concurrently. To bring the signal back to a useful level, the input power level must be increased. This, in turn, not only can cause photo-bleaching in the fluorophores at which one intends to look but also the surrounding area where the light is incident, just not collected. A method around this is to use two-photon excitation. Fluorescence from the two-photon effect depends on the square of the incident light intensity, which in turn, decreases approximately as the square of the distance from the focus. Because of this highly nonlinear (approximately fourth power) behavior, only those dye molecules very near the focus of the beam are excited, while the surrounding material is bombarded only by comparatively much fewer of the low energy photons, which are not of enough energy to cause photo bleaching. Multi-photon excitation requires highly skilled technicians and is somewhat expensive for clinical use. Because it acquires only a small area at once, the surface must be scanned in three dimensions for mapping.

Fluorescence Resonance Energy Transfer (FRET) can provide exquisite resolution of single chromophores. The resonance occurs when one fluorophore in an excited state transfers a portion of its energy to a neighboring chromophore. For this to take place, there must exist some overlap between the emission spectrum of the fluorophore to absorption spectrum of the chromophore (the frequency of the emission spectrum should be somewhat higher than the absorption spectrum of the chromophore). The process does not occur through photonic emission and absorption but through a dipole-dipole interaction. The strength of the interaction varies as $r^{-6}$. The Forster distance [see Forster, T Discuss. Faraday Soc. 27 7-29(1959)]is the distance at which the efficiency of the transfer is such that there exists equal probability that the fluorophore loses energy to radiative decay or dipole-dipole interaction. The Forster distance, essentially, is the threshold at which FRET will no longer exist for a given pair. Typically the Forster distance is between 3 and 6 nm [see Pollok & Heim "Using GFP in FRET-based Applications" Trends in Cell Biology 9 pp 57-60 (1999)].

By placing either of the complementary pair near the other, resolutions of less than the Forster distance can be attained. The problem with this technique in determining relative locations is that one of the pair needs to be located within the resolution tolerances desired for spatial mapping. This can be achieved by placing one of the pair on a probe used in either atomic force microscopy (AFM) or near-field scanning optical microscopy (NSOM). Another problem is that dipole-dipole interactions are dependent on the relative orientation of the two. To maximize signal from the interaction would require a 3D scan around one of the pair.

Atomic Force Microscopy (AFM) can be envisioned as a very small (usually metal) stylus dragged across a surface giving feedback as to the height, Z, of the stylus relative to the surface. Resolution can be as fine as the scanning step size (typically 5 nm). By scanning across the surface, X and Y coordinates are obtained provided that the origin remains fixed (i.e., that there is no drift in the translation stage due to thermal or other effects). There are many methods for ensuring that the stylus does not actually contact the sample but maintains very accurate resolution of the Z coordinate. Because only surface morphology is measured, differentiating several molecules can be extremely difficult unless the dimensions and orientations of those molecules are well known. A solution to this might be to add tags of discrete lengths or shapes, which could be bound indirectly to the molecules of interest. This method, however, would require that the tissue sample to be planar before the tags were bound to the surface.

To increase the information of AFM, one could use Near-Field Scanning Optical Microscopy (NSOM or SNOM). NSOM uses a principle similar to AFM in which a stylus is scanned over a surface providing topographical information. However, the stylus is a conductor of photons. By emitting light from the tip of the stylus, optical measurements such as fluorescence can be obtained. Most often, these styli are fiber probes that have tapered tips and then are plated with a conductive material (aluminum is most often chosen as its skin depth for optical radiation is quite low, about 13 nm at 500 nm) with a small aperture where the coating is broken. [See Betzig & Trautman "Near-Field Optics: Microscopy, Spectroscopy, and Surface Modification beyond the Diffraction Limit" Science 257 pp 189-195 (1992)]. Another approach is to use what are called "apertureless probes" [see Sanchez, Novotny and Xie "Near-Field Fluorescence Microscopy Based on Two-Photon Excitation with Metal Tips" Physical Review Letters Vol 82 20 pp 4014-4017 (1999)] where an evanescent wave is excited by bombardment with photons at the tip of a sharpened metal probe. Because the tip can be made very sharp (radii of 5 nm are achievable), resolutions can be correspondingly smaller. An associated problem with the "apertureless probes" is that the probe generates a white light continuum, which significantly decreases the signal to noise ratio.

By making the diameter (assuming a circular geometry) of the emission portion of the tip of the stylus very small (smaller than resolution desired) and keeping the tip to sample distance less than that distance, so that the diffraction is small, a nanometric light source is available. This light source can be used to excite fluorescence in the sample. Because the size of the source is very small and the scanning increments are also very small, highly resolved information on spatial locations of the fluorophores can be gleaned by inspection in the far field. Alternatively, the probe can be used for collection, measuring fluorescence or reflection or even transmission from illumination from the other side of the sample.

Because the aperture size in a conventional probe is so much smaller than the wavelength of the excitation light and only an evanescent mode is supported, very little light is transmitted through the aperture. Diffraction effects limit the effective collimated length from the aperture to less than diameter of the aperture. This, then, requires that the aperture be held below a maximum height above the surface of the sample. Ideally, a fixed height above the surface (usually less than 10 nm) is used for relative contrast measurements. The height of the aperture relative to the surface is kept constant by measuring the shear force on the tip of the probe or by optical methods and is modulated to maintain that height. For this reason, NSOM is particularly susceptible to vibrations and experimental work requires isolation platforms.

Scanning the surface takes a fair amount of time. Thermal drift in commercially available open and closed loop nanometric scanning stages is about 20-30 nm/min. [see Frohn, Knapp and Stemmer "True optical resolution beyond the Rayleigh limit achieved by standing wave illumination" Proceedings of the National Academies of Science Vol. 97, 13 pp 7232-7236 (2000)]. This can be severely limiting if scanning time is more than a few tens of seconds and resolution less than 50 nm is desired. If the surface is scanned for several different types of molecules, the required time to investigate a single cell becomes far too large for use in a clinical setting and would require multiple homings of the scanning stage. An approach to diminishing the scanning time may be to scan with multiple probes concurrently. This approach would be limited to just a few probes as on a small (20 micrometer by 20 micrometer) surface, the relatively large size of the probes' bodies would interfere mechanically with each other.

U.S. Pat. Nos. 5,973,316 and 6,052,238 issued to Ebbesen et al. of the NEC Research Institute, Inc. (which patents hereby are incorporated herein by reference) describe a NSOM device which employs an array of subwavelength apertures in a metallic film or thin metallic plate. Enhanced transmission through the apertures of the array is greater than the unit transmission of a single aperture and is believed to be due to the active participation of the metal film in which the aperture array is formed. In addition to enhancing transmission, the array of apertures reduces scanning time by increasing the number of nanometric light sources.

A subsequent patent issued to Ebbesen et al, U.S. Pat. No. 6,236,033 (which patent hereby is incorporated herein by reference), discloses that other structures forming a periodic surface topography on one surface of a metallic film may be employed to enhance the light transmission through one or more apertures in the film. This patent states that the periodic surface topography can take the form of a periodic array of holes, only some of which pass completely through the film, while other periodic surface topography arrangements employ regular, periodic ridges or depressions in the film surface. U.S. Pat. No. 6,236,033 further states that light transmission from one or more apertures in a periodic topography formed by periodic surface features is effective so long as a plurality of periodic surface features (i.e., at least two) are present in addition to a given aperture, and that the arrangement is effective with as few as two periodic surface features adjacent to the aperture.

SUMMARY

The present invention contemplates a different technique to achieve sub-Rayleigh criterion resolution, which is here called "Surface Plasmon Enhanced Illumination" (SPEI). SPEI is related to NSOM in that nanometric light sources are created by subwavelength apertures. By applying the principles of the present invention, a significant reduction in the size of the area illuminated by each aperture is achieved, resulting in significantly improved resolution.

The present invention takes the form of methods and apparatus that employ novel physical structures to provide nanometric spot or line illumination. In accordance with the invention, one or more apertures are formed through a first planar conductive material. Each aperture (which may be either a hole or a slit) has at least one cross-sectional dimension which is less than the wavelength of light which is incident to the planar material. In accordance with a feature of the invention, the structure includes means for confining the electronic excitation induced in that portion of the planar surface near the end of the aperture from which the light exits.

For purposes of the present disclosure, the conductive plane also may be referred to as a "metal film," wherein the term "metal" denotes a material that exhibits a significantly metallic behavior at frequencies corresponding to the incident light. The conductive plane that receives the incident light may be placed on one outer surface of a dielectric material or other material that exhibits a significantly non-metallic behavior at frequencies corresponding to the incident light. The dielectric (or non-metallic) material's interface with the conductive plane that receives the incident light establishes a substantially different effective dielectric function in that interface than that of the conductive plane that receives the incident light. This difference in effective dielectric function prevents the excitation of large densities of surface plasmons in the non-illuminated plane of the metal if monochromatic light is used at the resonant wavelength of the illuminated metallic plane. Therefore light should not be substantially emitted from the non-illuminated metallic plane.

Alternatively, the sidewalls of the aperture may be conductive to conduct excitation currents and act as a pseudo-waveguide for the light traveling through the aperture. At the exit end of the aperture, the amount of exposed conductive material is limited to an area immediately surrounding the hole exit by a dielectric material, or by a groove cut into the surface of the conductive material at the exit plane to a depth substantially deeper than the skin depth of the induced excitation and of such width and spacing to prevent an unwanted resonance of surface plasmons in that surface.

Alternatively, the conductive plane that receives the incident light may take the form of a "good metal" layer with a "bad metal" layer (i.e., a material exhibiting significantly non-metallic behavior at frequencies corresponding to the incident radiation) having significantly different dielectric properties being sandwiched between the good metal layer and a dielectric substrate. The bad metal layer is preferably opaque to the light to be emitted from the surface of the good metal and its resonance (as determined by its dielectric function, the surface roughness and the dielectric functions of the materials on either side of the bad metal layer) should be very different from the resonance of the "good" metal, such that at desired frequency, light transmitted is emitted only from the holes and not from the exit surface of the array. The insulating dielectric substrate ensures that there can be no surface plasmon excitation from the good metal layer through the light barrier. When a bad metal layer is used that is both opaque to light and has sufficiently different dielectric properties relative to the good metal to eliminate resonant coupling, the dielectric insulator may be eliminated.

The present invention substantially reduces, compared to an array of subwavelength apertures in a monometallic film such as those described by Ebbesen et al., the size of the area of illumination produced by each aperture using the combination of a metallic layer on which surface plasmons are induced by incident light and surface composed of a material of substantially different dielectric function, such as an insulator or a different metal, so that the excitation of the surface plasmons in the light emitting surface in the exit surface layer will be different than those excited in the metallic layer that is excited by the incident light, and only the light from the decaying resonant surface plasmons of the exit layer will emit from that surface. The photons associated with the resonance of the incident or upper surface will be constrained to exit from the hole itself or from the walls of the hole.

In accordance with the invention, the light barrier comprises an illuminated surface comprising a continuous conductive metallic layer in combination with an exit layer having substantially different dielectric properties. One or more apertures through the barrier (one or more holes or slits) then form "photonic funnels" through the barrier. Note that confining or eliminating electronic surface excitation on the surface opposite to the illuminated surface works with a single aperture as well as an array of apertures.

The invention may advantageously take the form of an array of apertures (holes or slits) formed in a structure comprising a dielectric substrate coated with a conductive metal film on one or both surfaces, or by a thick metallic film, and which further incorporates means for confining the electronic surface excitation to an area immediately adjacent to the apertures where light exits the structure. The means for confining the electronic surface excitation preferably takes the form of a layer of material having dielectric properties that differ substantially from those of the illuminated metal layer, and may consist of a dielectric insulator, a "bad metal" having different dielectric properties, grooves or surface irregularities at the exit surface, or a combination of these. The structure which confines the electronic surface excitation restricts the size of the spot or line of illumination from each aperture, and the use of an array of apertures, or an array of surface irregularities on the metal film, increases the intensity of the illumination from each aperture.

Applicants also have recognized and appreciated that, contrary to the teachings of U.S. Pat. No. 6,236,033 to Ebbesen et al., a periodic surface topology is not necessarily required to achieve enhanced transmission through a sub-wavelength aperture. Rather, in other embodiments of the present disclosure, a resonance condition that supports surface plasmon enhanced generation of radiation may be facilitated by one or more features that form a non-periodic structure together with an aperture in a planar conductive material such as a metal film.

For purposes of the present disclosure, according to various exemplary embodiments, a "non-periodic structure" refers to a structure constituting a resonance configuration that includes only two elements (at least one of which is an aperture) proximate to each other in a metal film. In various implementations of this embodiment, examples of a single feature in addition to an aperture to form such a resonance configuration include, but are not limited to, single topographic features such as another aperture, a depression in the metal film, a single annular groove surrounding the aperture, a protrusion that extends outwardly from the surface of the metal film, and a single raised ring surrounding the aperture. Each of these features causes a variation in a dielectric function along the surface of the metal film proximate to the aperture.

For purposes of the present disclosure, in other embodiments, a "non-periodic structure" also refers to a resonance configuration that includes three or more elements (including an aperture) proximate to each other in a metal film, in which any two distances between adjacent elements is not equal, and/or a shape and/or dimension of any two elements is not equal. Stated differently, a non-periodic structure does not have equidistant spacing between three or more elements of the structure, and/or three or more identically shaped and/or dimensioned objects along a surface of a metal film. In various implementations of this embodiment, examples of one or more features in addition to a single aperture to form such a resonance configuration include, but are not limited to, one or more topographic features (protrusion(s), depression(s), groove(s), raised ring(s), etc.) having different shapes and/or dimensions from the aperture, as well as one or more edges of a metal film in which the aperture is formed. For example, an aperture may be defined in and through a metal film having an otherwise smooth surface (no significant topological features) that terminates at one or more edges spaced at a resonant distance from the aperture. Again, each of the foregoing features causes a variation in a dielectric function along the surface of the metal film proximate to the aperture.

The various concepts disclosed herein relating to SPEI methods and apparatus may be applied to advantage in a variety of applications including, but not limited to, optical data storage, microscopy, and lithographpy.

For example, in an optical data storage device, several arrangements may be devised for combining an SPEI apparatus including an aperture array with some medium for data storage. A light source, such as a laser, may be directed onto the front surface of the hole array which collects and funnels the array of light onto an optical storage medium. The bit value stored at each position in the storage medium controls the propagation of light through the storage medium to an adjacent pixel position in a charge coupled device (CCD) or other area detectors. A translation mechanism effects movement of the storage medium relative to the hole array in incremental steps, with each step distance being equal to the aperture size. In an alternative arrangement, data may be represented by illumination levels, such as gray scale values or color levels, and optical means may be used in place of or to supplement the mechanical translation mechanism.

The well defined and highly concentrated areas of illumination created by employing SPEI methods and apparatus disclosed herein provide significant advantages also in microscopy and lithography applications. For example, the confined illumination patterns produced in accordance with the invention may be used to construct a "Surface Plasmon Enhanced Microscope" (SPEM) exhibiting markedly improved resolution, to construct an optical data storage device capable of storing larger amounts of data in optical storage media with much higher data access rates than is achievable with current optical data storage devices, and to provide a high throughput photolithography technique that can be applied to advantage in semiconductor fabrication and patterning for self-assembly and biological applications.

In sum, as discussed in greater detail below, one embodiment of the disclosure is directed to an apparatus, comprising a metal film having a first surface and a second surface, and at least one resonance configuration formed in the metal film. The at least one resonance configuration comprises an aperture extending between the first surface and the second surface and at least one feature that forms a non-periodic structure together with the aperture. The at least one feature causes a variation in a dielectric function along the first surface proximate to the aperture. The aperture and the at least one feature are configured so as to cooperatively facilitate a resonance condition for surface plasmon enhanced radiation generated by the apparatus, based on incident radiation, when present, that irradiates the first surface of the metal film.

Another embodiment is directed to an apparatus, comprising a metal film having a first surface and a second surface, and at least one resonance configuration formed in the metal film. The at least one resonance configuration comprises an aperture extending between the first surface and the second surface, and a single feature that causes a variation in a dielectric function along the first surface proximate to the aperture. The aperture and the single feature are configured so as to cooperatively facilitate a resonance condition for surface plasmon enhanced radiation generated by the apparatus, based on incident radiation, when present, that irradiates the first surface of the metal film.

Another embodiment is directed to an apparatus, comprising a metal film having a first surface, a second surface, and at least one edge, and an aperture extending between the first surface and the second surface. The aperture and the at least one edge are configured so as to cooperatively facilitate a resonance condition for surface plasmon enhanced radiation generated by the apparatus, based on incident radiation, when present, that irradiates the first surface of the metal film.

Another embodiment is directed to an apparatus, comprising a metal film having a first surface and a second surface, and at least one resonance configuration formed in the metal film and configured so as to facilitate a primary resonance condition for surface plasmon enhanced radiation generated by the apparatus, based on incident radiation, when present, that irradiates the first surface of the metal film. The at least one resonance configuration further is configured to preclude conflicting resonance conditions other than the primary resonance condition.

It should be appreciated that all combinations of the foregoing concepts and additional concepts discussed in greater detail below are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

DETAILED DESCRIPTION

As described in U.S. Pat. Nos. 5,973,316 and 6,052,238 issued to Ebbesen et al., enhanced light transmission occurs through an array of apertures in a metal film due to surface plasmons induced in the conductive film by the incident light.

Figure 1:
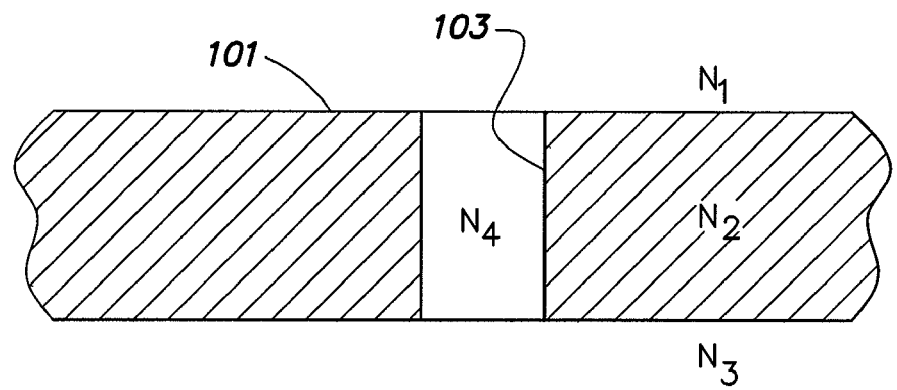
FIG. 1 is a cross-sectional view of an aperture through a metallic film, the film being substantially thicker than the skin depth within which an optically induced electronic excitation occurs (i.e., the skin depth of surface plasmons), and the aperture having a diameter less than the wavelength of the incident light.
Figure 2:
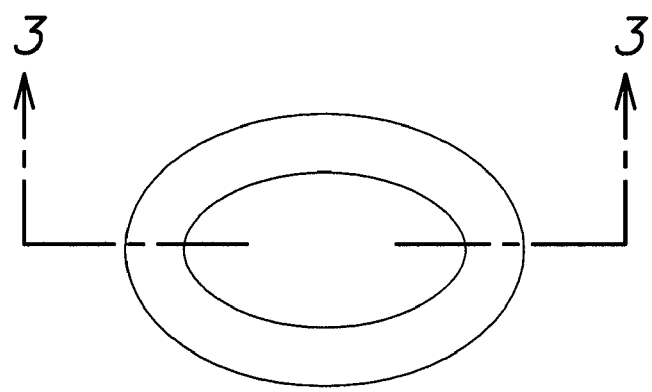
FIG. 2 is a view illustrating the approximate size of the oblong-shaped area illuminated by the light transmitted through the aperture in the film shown in FIG. 1.

FIG. 1 shows a cross section of an optically thick metal film 101. The term "optically thick" means that the thickness of the film 101 is greater than two times the skin depth of surface plasmons induced on the surface of the film irradiated by incident radiation. For all essential purposes, this means that there is no direct coupling of the surface plasmons (coherent collective excitations of electrons) at the upper surface (the interface between media of index $N_1$ and $N_2$) and the lower surface (the interface between media of index $N_3$ and $N_2$). In a typical case, the indices $N_1$, $N_3$, and $N_4$ are equal while $N_2$, the index of the metal film 101, is substantially different and the metal film 101, unlike the surrounding material, is a conductor of electronic charges.

If the array spacing and the dielectric functions and thickness of the metals and substrates are tailored to attain a high transmission, a significantly higher power density than that transmitted through the single aperture probe used in NSOM (a ratio of about one million per aperture for a 50 nm holes) can be delivered through the apertures. This substantially increases the signal to noise ratio of surface plasmon enhanced microscopy (SPEM) over the NSOM at normal resolutions and is allows a smaller hole size to be used, providing better resolution and dramatically decreasing the dwell time required for an adequate signal to be received.

Unfortunately, the coupling (indirect or direct) between the surfaces of the film 101 seen in FIG. 1 have effects that adversely affect desired resolution. Sonnichsen et al., "Launching surface plasmons into nanoholes in metal films", App. Phys. Lett. 76, 140-142 (2000) show that, when gold, silver or aluminum films are struck with plane polarized light, surface plasmons are induced in the direction of the polarization. When the plasmons encounter a hole, the coupling to the other side results in light emitted in a prolate shape of a major dimension of about an order of magnitude larger than the hole size. The prolate shape is caused by the radiative decay of the surface plasmons and is a function of the dielectric function of the metal and the wavelength of the incident light and if significant surface roughness exists, the distance between the elements of roughness on that plane.

With a simple isotropic periodically perforated metal film, two potential problems are encountered. First, for use in a microscope and other applications (e.g. optical data storage and photolithography) where small sources of light (high resolution) are required, the existence of the associated prolate pattern diminishes resolution in one dimension severely. Second, the array spacing would have to be such that patterns did not interfere or overlap. Achieving the appropriate spacing would in turn cause the wavelengths at which the surface plasmons are resonant to be shifted, resulting in resonant wavelengths of lower energy. For the excitation of commonly available fluorophores, multi-photon (probably three or four) excitation would be required. Of course, the prolate pattern could simply be accepted and the resolution in the direction of the polarization (along the major axis of the pattern) would default to that dictated by the Rayleigh criterion for that wavelength and numerical aperture.

If a smaller spot illumination size (a nanometric light source) is required, the prolate shape generated from the geometry shown in FIG. 1 is undesirable. If the incident light is polarized, the long dimension of the pattern shape is probably only loosely dependent on the hole size and more dependent on the surface roughness, since rougher surfaces act as very small antennae, which cause surface plasmons to decay, spatially, more rapidly than would be the case if the film surface were smooth. Moreover, the frequency of the light will also affect the pattern shape. Note also that the preferred shape of the intensity pattern for spot illumination should exhibit a step function rather than the extended somewhat Gaussian pattern that is seen along the major axis of the prolate shape.

In accordance with the present invention, novel structures are used to minimize or eliminate the prolate pattern described above. If the emitting surface (bottom) is no longer continuous but is instead constructed to constrain the propagation of surface plasmons to the immediate vicinity of the aperture, the size of the resulting area of illumination is significantly reduced. If the illuminated surface (top) is left as a continuous conductor with an array of circular holes in it and the bottom is segmented as described above, a photonic funnel can be created. To minimize the effective broadening of the holes due to surface plasmons on the bottom plane, it may be desirable to create a very sharp edge at this point in either a conducting wall or in an insulator with less available charge to minimize any surface-plasmons/photon interaction. It is important to note that the insulator (in the case of a semiconductor) should have a band gap significantly larger than the frequency of the photons, which will be propagating through it.

Figure 4:
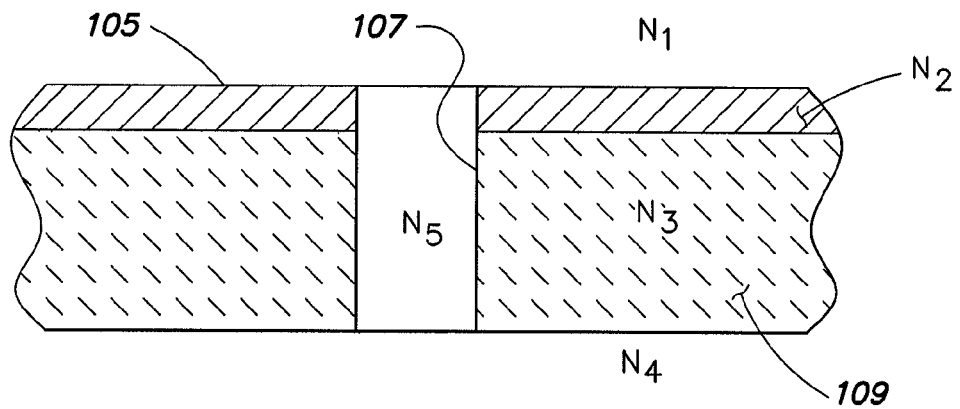
FIG. 4 is a cross-sectional view of a thin metallic film that covers a non-metallic substrate material with an aperture through both the metal film and substrate having a diameter less than the wavelength of the incident light.

A first improved geometry for the hole array that produces a smaller illumination pattern is shown in FIG. 4 of the drawings. A thin metal conductive film 105 exhibiting the index $N_2$ is affixed to a substrate 109 constructed of a dielectric material having the index $N_3$ and a bandgap that is larger than the frequency of the illumination of light. The dielectric substrate 109 can be constructed of a material that is transparent (but need not be) to light at the frequency employed, such as quartz or glass. Note that the aperture 107 need not go though the dielectric substrate if it is transparent, and such a structure may be easier to fabricate. The substrate should have a small index of refraction $N_3$ compared to the index of the metal $N_2$. Note also, as discussed later in connection with FIG. 20, that a "bad metal" having poor conductivity at these frequencies (such as tungsten) may be used in place of the dielectric 109 in combination with a "good metal" illuminated layer (such as aluminum). In fluorescence studies, if multi-photon excitement is employed, the bandgap should be larger than the sum of the photonic energies of the photons that would be simultaneously absorbed by the fluorophore. The thin layer of conducting material 105 should be thicker than the surface plasmon skin depth of the metal at frequencies corresponding to the incident radiation. The geometry and composition of the heterogeneous structure seen in FIG. 4 should be chosen so that a maximum of transmission of illumination occurs though the hole 107 at the chosen illumination wavelength. A tunable or broad band light source may also be used to tune the wavelength to predetermined hole dimensions.

Figure 5:
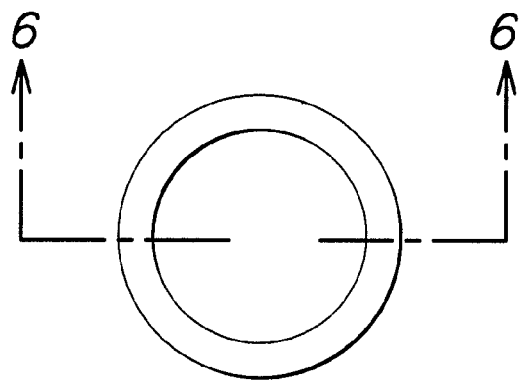
FIG. 5 is a view illustrating the approximate size of the circular area illuminated by the light transmitted through the aperture in structure shown in FIG. 4.
Figure 6:
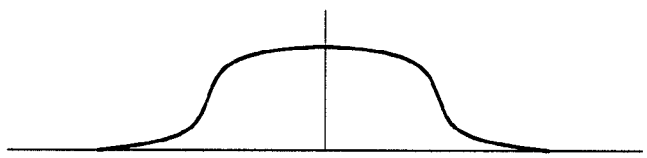
FIG. 6 is a graph illustrating the illumination intensity in the illuminated area taken along the line 6-6 of FIG. 5.

The advantage of the geometry shown in FIG. 4 over that presented in FIG. 1 results from the fact that there is no coupling of plasmons from the upper surface of the film 105 to the lower surface of the dielectric material 109. This reduced coupling creates a smaller and more defined illumination pattern with steeper side slopes as illustrated in FIGS. 5 and 6. It is unclear, though, what happens to the energy at the corner interface of the hole 107, the metal film 105 and the dielectric substrate 109, that is, at the boundary of the materials having the indices $N_5$, $N_2$ and $N_3$. If $N_1$, $N_4$ and $N_5$ are not all substantially equal to one (1.0), combinations of differing indices could be used to tailor the transmission of the array apertures for a specific wavelength or method of illuminating the structure. For example, N could be the index associated with an optical fiber, which would be coupled to a remote light source.

Figure 3:
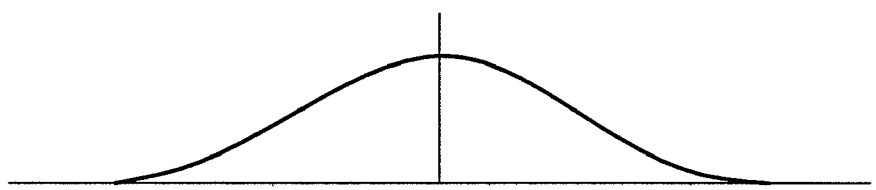
FIG. 3 is a graph illustrating the illumination intensity in the illuminated area taken along the line 3-3 of FIG. 2.
Figure 7:
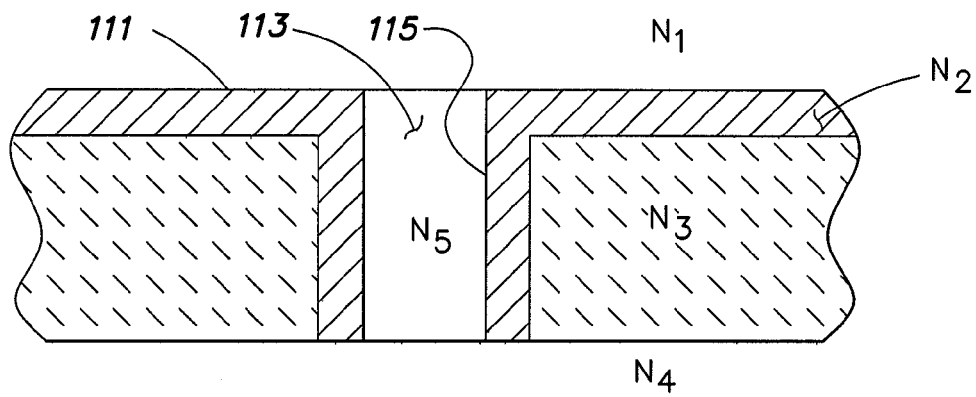
FIG. 7 is a cross-sectional view of a thin metallic film that covers the surface of a non-metallic substrate material as well as the sidewalls of an aperture through the substrate with the aperture having a diameter less than the wavelength of the incident light.
Figure 8:
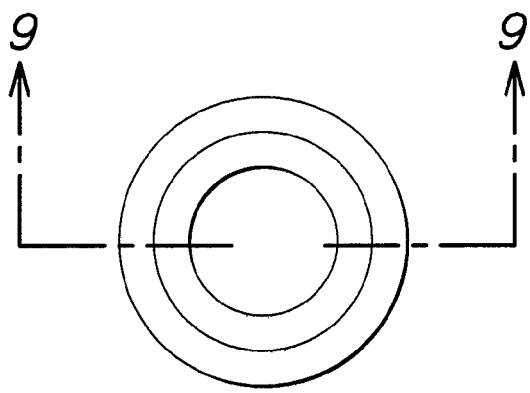
FIG. 8 is a view illustrating the approximate size of the circular area illuminated by the light transmitted through the aperture in the structure shown in FIG. 7.
Figure 9:
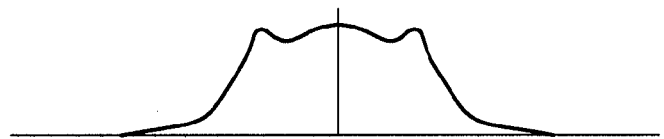
FIG. 9 is a graph illustrating the illumination intensity in the illuminated area taken along the line 9-9 of FIG. 8.

A second hole array structure for reducing the size and increasing the density of the spot illumination is shown in FIG. 7. As before, the structure of FIG. 7 presents at its upper surface a continuous conducting thin film metallic film 111 having the index $N_2$. The structure differs from that shown in FIG. 4 in that the metallic coating is continued into the interior of the hole 113 as seen at 115. If the thickness of metal layer 115 in the hole interior were greater than skin depth, the effects seen in optically thick metal films as shown in FIG. 1 would be duplicated from the standpoint of optical transmission through the holes. However, a smaller and more concentrated output light pattern is achieved by limiting the propagation length of surface plasmons at the exit surface to the thickness of the film in the hole. Limiting the size of the excited surface area surrounding the hole exit produces a concentrated, circular light pattern as seen in FIG. 8 rather than prolate pattern seen in FIG. 3, thus limiting the size of the light source in only one of its two dimensions. As is the case with the structure shown in FIG. 4, the indices $N_1$, $N_4$ and $N_5$ may be equivalent to 1.0 in the simplest configuration but other combinations be used to tune the holes for a specific resonance. FIG. 9 graphs the steeply skirted intensity distribution expected across the circular light pattern along the line 9-9 of FIG. 8.

Figure 10:
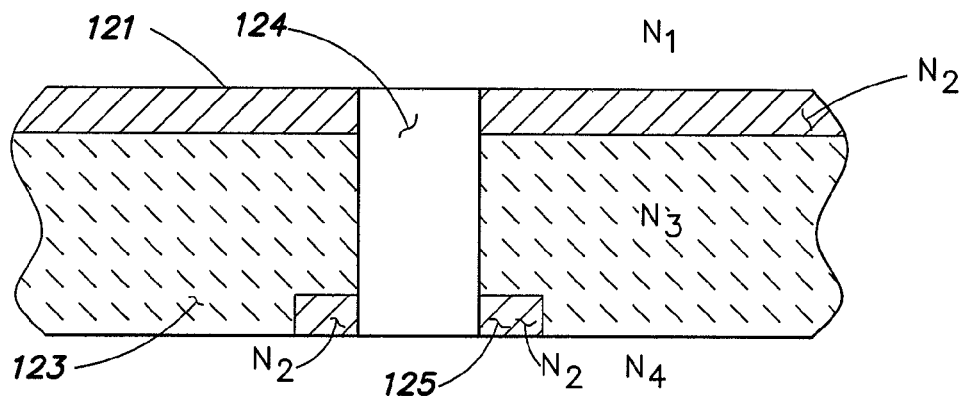
FIG. 10 is a cross-sectional view of a thin metallic film which covers a non-metallic substrate material, an aperture through the substrate, and a thin, annular metallic ring surrounding the aperture on the opposing surface of the substrate, with the aperture having a diameter less than the wavelength of the incident light.
Figure 11:
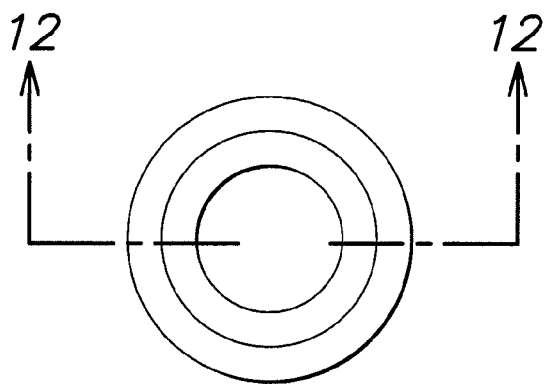
FIG. 11 is a view illustrating the approximate size of the circular area illuminated by the light transmitted through the aperture in the structure shown in FIG. 10.
Figure 12:
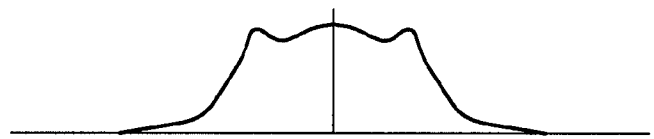
FIG. 12 is a graph illustrating the illumination intensity in the illuminated area taken along the line 11-11 of FIG. 10.

A third structure that may be used as a source of concentrated light is shown in FIG. 10. As in the structures shown in FIGS. 4 and 7, a thin metallic film 121 covers the upper surface of a dielectric substrate 123. A hole 124 though the film 121 and the substrate 123 is not lined with a conductor as in FIG. 7. Instead, an annular ring 125 of conductive material surrounds the exit end of hole 124 at the lower surface of the substrate 123. The conductive ring 125 increases the coupling with the film 124 to improve light transmission though the hole 124 but does not permit the surface excitations surrounding the hole exit to spread beyond the outer periphery of the ring 125, thereby again achieving the more concentrated, steep skirted output light pattern shown in FIG. 11 and 12.

Figure 13:
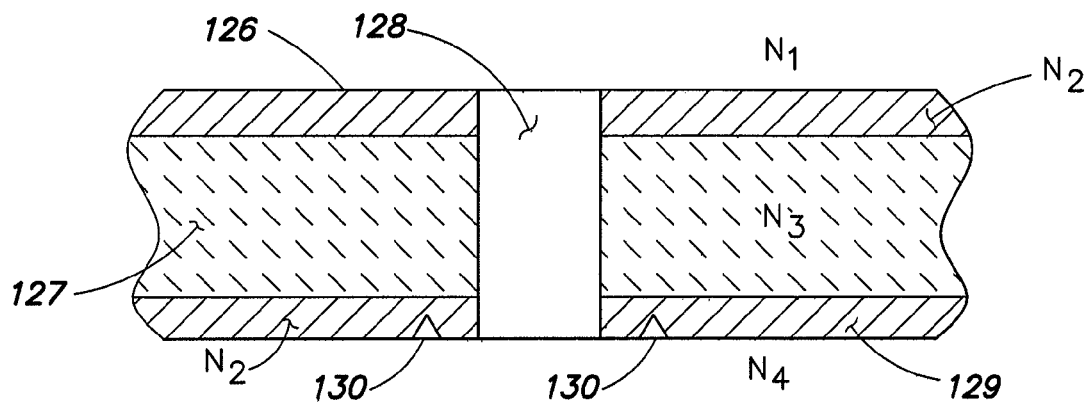
FIG. 13 is a cross-sectional view of a hole structure in which a thin metallic film which covers both surfaces of a non-metallic substrate material, and an annular notch is cut into the film at the exit surface which surrounds and is spaced from the hole.
Figure 14:
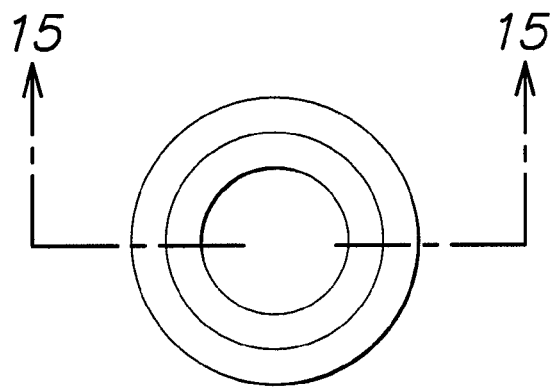
FIG. 14 is a view illustrating the approximate size of the circular area illuminated by the light transmitted through the aperture in the structure shown in FIG. 13.
Figure 15:
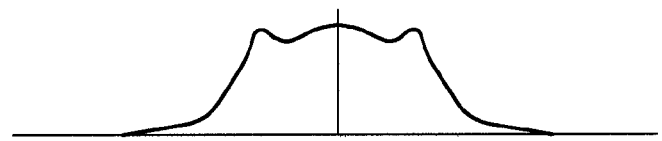
FIG. 15 is a graph illustrating the illumination intensity in the illuminated area taken along the line 15-15 of FIG. 14.

FIG. 13 shows still another structure in which a dielectric substrate 127 is coated on its upper surface with a metallic film 126 and on its lower surface with a metallic film 129. The hole 128 passes through both films and through the substrate and its side walls are not coated. An annular groove seen at 130 is formed in the film 129 and surrounds and is spaced from the hole 128. The groove has a nominal outside diameter of 25 nm and inside diameter of 20 nm. The depth of the groove must be at substantially deeper than the surface plasmon skin depth of the material, i.e., deep enough to act as insulator with respect to induced surface excitations. The groove may have any convenient shape and may be rectangular or triangular as well as semi-circular. Note that, by using a groove of the type shown in FIG. 13, an optically thick metallic structure may be used instead of a dielectric substrate, so that the hole is effectively lined by a conductor. In both cases, the groove serves to contain the coupled electron excitation within a surface area close to the hole exit, thereby preventing unwanted spreading of the illumination pattern. The illumination pattern produced by the hole and groove configuration of FIG. 13 is depicted in FIGS. 14 and 15.

Figure 16:
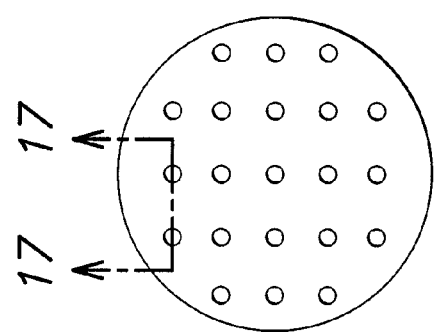
FIG. 16 is an end plan view of a multi-aperture probe constructed in accordance with the invention.
Figure 17:
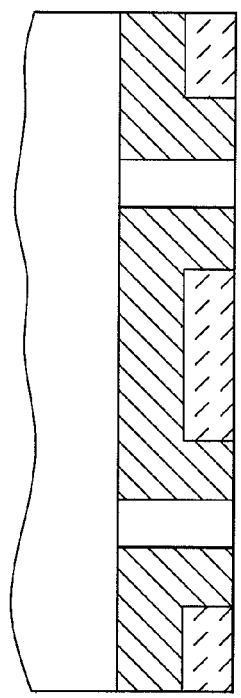
FIG. 17 is a cross sectional view of the probe seen in FIG. 16 take along the line 17-17.
Figure 18:
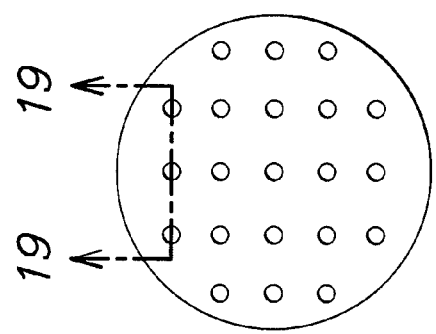
FIG. 18 is an end plan view of an alternative structure for the multi-aperture probe constructed in accordance with the invention.
Figure 19:
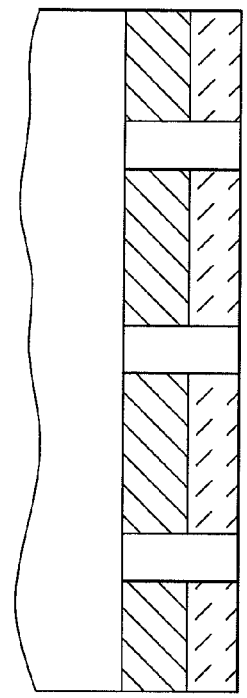
FIG. 19 is a cross sectional view of the probe seen in FIG. 18 taken along the line 19-19.

The principles of the invention may be used to construct a multi-aperture probe (MAP) which may be used to advantage in a scanning microscope, for example. FIGS. 16 and 17 illustrate a MAP structure using holes with electrically conducting sidewalls of the type discussed earlier in connection with FIGS. 7 and 13, while FIGS. 18 and 19 show the construction of a MAP having holes whose sidewalls are in part non-conducting as previously discussed in connection with FIGS. 4 and 10 of the drawings.

As also discussed above, another approach to eliminating the prolate pattern is to align the polarization with a slit. If the material through which the photons are propagating has low charge availability (as in slit), there can be very few or no surface plasmons. Also, the propagation of light is supported along the slit and throughput should be higher for an array of slits versus an array of circular holes of the same area. Work done on slits much smaller than the transmitted wavelength (32 nm slit) [see Astilean, Lalanne and Palamaru "Light transmission through metallic channels much smaller than the wavelength" Optics Communications 175 265-273 March 2000] in optically thick metal films shows peaks in the NIR and visible transmission versus incident wavelength curves with maxima in the order of 80% efficiency for the plate with a grid spacing of 900 nm. For the strongest peak, 1.183 micrometers, this is an extraordinary amount in that almost 10 times the amount of light impinging on the slits is transmitted through them. Also reported are slits of 10 nm widths, which when excited at resonance, achieve 10% efficiency. Astilean et al. conclude that the resonance condition is not only a function of the surface plasmon resonance but that the metallic wall linings of the slits act as Fabry-Perot cavities and that greatly enhanced transmissions occur when the slit satisfies the Fabry-Perot resonance condition [see Born, M. and Wolf, E. Principles of Optics. Cambridge University Press 6th ed. 1980 p. 326] with an effective index of refraction which depends strongly on the slit width and material.

Figure 20:
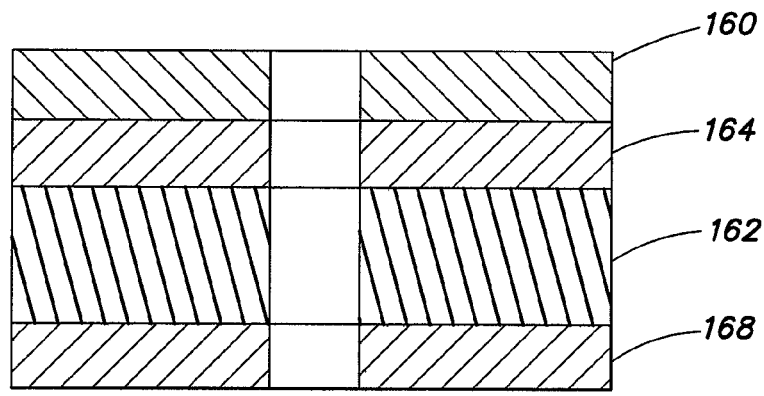
FIG. 20 is a cross sectional view of an alternative light barrier structure employing "good" and "bad" metal layers.

FIG. 20 shows still another configuration which utilizes the principles of the present invention. In this arrangement, the light barrier is composed of three different materials: a "good" metal layer 160 over a substrate consisting of an insulator 162 sandwiched between two layers of "bad metal" 164 and 168. As with the other structures, the "good" metal used in layer 160 is one in which the surface plasmons will decay over a relatively long distance as determined by the surface roughness of the film 160 (which includes the holes) and the relative values of the real and imaginary parts of the dielectric function of film 160 (where a small imaginary part provides a long delay decay length). In contrast, the "bad" metal used in the layers 164 and 168 has a dielectric function with a large imaginary part so that the surface plasmons decay more quickly over a relatively short decay length.

The "bad" metal used in layers 164 and 168 preferably exhibits two additional properties which make a significant contribution to the creation of nanometric light sources.

First, the "bad metal" should be opaque to the light emitted from the surface of the "good" metal in thin films. Second, the resonance of the "bad" metal layer(s) should be very different than that of the "good" metal. The resonance of the metal layers is determined only by the real part of the dielectric function for metal, the surface roughness of the metal layers, and the dielectric functions of the materials on either side of the metal layer.

The insulator 162 ensures that there can be no surface plasmon communication from top to bottom through bulk plasmons or any other direct electronic interaction. Note, however, that the presence of the insulator 162 may not required if the bad metal satisfies the criteria expressed above; that is, is opaque to light emitted from the good metal layer and has a resonance that is very different from the good metal layer.

For the all of the structures described in connection with FIGS. 4-20, the diameter of the hole should be between about 2 nm and 50 nm. The metallic film layers should, as noted earlier, be at least skin depth of the surface plasmon electronic excitation and may be formed, for example, from gold, silver, aluminum, beryllium, rhenium, osmium, potassium, rubidium, cesium, rhenium oxide, tungsten oxide, copper or titanium (if employed at the appropriate frequencies). Suitable dielectric and "bad metal" substrate materials include germanium, silicon dioxide, silicon nitride, alumina, chromia, some forms of carbon and many other materials including some of the metals listed as "good metals" at the appropriate frequencies. The aperture array with sub-wavelength holes may be fabricated using available focused ion beam (FIB) milling techniques.

Any of the structures described above in connection with FIGS. 4-20 can be modified so as to facilitate a resonance condition to generate surface plasmon enhanced radiation from a single aperture. For example, in one such implementation, all but the central aperture in a set of apertures would be changed from apertures that go through the barrier to elements of surface roughness (dimples or protuberances) that are deeper than the surface plasmon skin depth and the same diameter as the aperture. Alternatively, the dimples surrounding the central aperture can be replaced with an annular groove or raised ring having a width equal to the emitting hole diameter and a depth (or height) greater than the surface plasmon skin depth. This technique allows the extraordinary transmission to be retained while only providing emission from the central aperture. In one exemplary application, this central aperture may be employed to generate a single light beam that is used to write patterns in photoresist to perform lithography.

Figure 21:
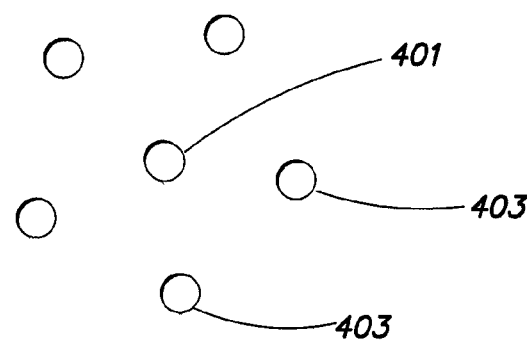
FIGS. 21 and 22 are plan views of the location of surface patterns surrounding a central aperture used to enhance the illumination from the central aperture.
Figure 22:
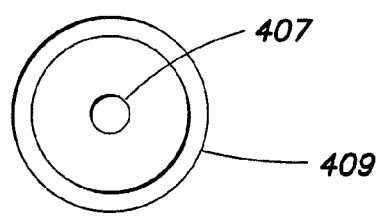

Some exemplary structures having only a single aperture are shown schematically in FIGS. 21 and 22. FIG. 21 illustrates a hexagonal pattern of apertures (one emitting aperture 401 surrounded by six dimples 403), where the relationship between a resonance condition and the spacing of features (i.e., the relationship that establishes the maximum wavelength at which photons in the incident radiation are resonant with surface plasmons in the metal film), assuming normal incidence of the incident radiation to the irradiated plane of the metal surface, is governed generally by the equation:

$$\lambda_{\max} = a_o \left( \frac{4}{3}(i^2 + ij + j^2) \right)^{-\frac{1}{2}} \left( \frac{\varepsilon_1 \varepsilon_2}{\varepsilon_1 + \varepsilon_2} \right)^{\frac{1}{2}}, \qquad (1)$$

where $\lambda_{max}$ is the maximum wavelength corresponding to the resonance condition, $\epsilon_1$ and $\epsilon_2$ are the real portions of the respective dielectric constants for the metal and the surrounding medium through which the incident radiation passes prior to irradiating the metal film, and $\alpha_o$ is the lattice constant (spacing between dimples/protrusions/apertures). The indices i and j are integers characterizing a particular branch of the surface plasmon dispersion (See Raether, Heinz "Surface Plasmons on Smooth and Rough Surfaces and on Gratings" Springer Tracts in Modern Physics v. 111, Springer-Verlag, Berlin 1988).

Lattice or array patterns other than the hexagonal pattern illustrated in FIG. 21 are permissible according to equations similar to Eq. (1) above, in which the integer indices i and j are modified for the specific lattice type. For example, the maximum wavelength corresponding to the resonance condition in a square array, assuming normal incidence of the incident radiation to the irradiated plane of the metal surface, is governed generally by the equation:

$$\lambda_{max} = a_o (i^2 + j^2)^{-\frac{1}{2}} \left( \frac{\varepsilon_1 \varepsilon_2}{\varepsilon_1 + \varepsilon_2} \right)^{\frac{1}{2}}. \quad (2)$$

If the square array is reduced to a linear array (i.e., a "one-dimensional grating" in which a center aperture is flanked, along a single axis, by dimples or protuberances), the index j in Eq. (2) above would be zero, and the equation reduces to:

$$\lambda_{max} = \frac{a_o}{i} \left( \frac{\varepsilon_1 \varepsilon_2}{\varepsilon_1 + \varepsilon_2} \right)^{\frac{1}{2}}, \quad (3)$$

in which the parameter $\alpha_o$ may be thought of as a grating constant in a one dimensional implementation (as opposed to a "lattice" constant, as indicated above for the two dimensional examples). As noted above, in each of Eqs. (1) through (3), essentially normal incidence of the incident radiation to the irradiated surface of the metal film is assumed. It should be appreciated, however, that these equations may be appropriately modified in a known fashion to account for the effects of non-normal incidence on the maximum wavelength corresponding to a resonance condition. More generally, it should be appreciated that Eqs. (1) through (3) represent suitable working models for the observed resonance behavior of the corresponding resonance configurations, but that resonance behaviors may be more precisely modeled via a somewhat more complicated and detailed mathematical analysis of the underlying physics.

While the above configurations discussed above in connection with Eqs. (1) through (3), and exemplified by the hexagonal pattern shown in FIG. 21, provide examples of single aperture devices involving a number of periodically arranged features (i.e., a periodic surface topology) proximate to the aperture, other embodiments of the present disclosure relate to resonance configurations involving only a single aperture and a single feature disposed proximate to the aperture. For example, FIG. 22 shows an alternative arrangement for facilitating a resonance condition according to yet another embodiment, in which a single emitting aperture 407 is surrounded by a single annular groove 409. In one aspect, a width of the annular groove is equal to the diameter of the emitting hole. In another aspect, a depth of the single annular groove should be greater than the skin depth of surface plasmons induced by the incident radiation. In yet another aspect, a single raised ring may be employed as an alternative to the single annular groove 409. Using such a resonance configuration in which the aperture 407 is at the center of a single annular groove or single raised ring, the maximum wavelength corresponding to the resonance condition (again assuming normal incidence of the incident radiation to the irradiated plane of the metal surface) is governed generally by the equation:

$$\lambda_{max} = \rho \left( \frac{\varepsilon_1 \varepsilon_2}{\varepsilon_1 + \varepsilon_2} \right)^{\frac{1}{2}}, \quad (4)$$

in which $\rho$ denotes the radius of the annular groove or raised ring from the centrally positioned aperture within the annular groove/raised ring.

The resonance configuration shown in FIG. 22 represents a non-periodic structure that includes only two elements (at least one of which is an aperture) proximate to each other in a metal film. Applicants have recognized and appreciated that a periodic surface topology (as represented by the configuration of FIG. 21) is not necessarily required to achieve enhanced transmission through a single aperture. Rather, in other embodiments of the present disclosure (e.g., as illustrated in FIG. 22), a resonance condition that supports surface plasmon enhanced generation of radiation may be facilitated by one or more features that form a non-periodic structure together with an aperture in a planar conductive material such as a metal film.

In other embodiments discussed below, examples of a single feature in addition to an aperture to form such a resonance configuration include, but are not limited to, single non-annular topographic features such as another aperture, a depression in the metal film, and a protrusion (protuberance) that extends outwardly from the surface of the metal film. In one aspect, non-annular topographic features may have dimensions in cross-section on the order of the aperture. Like the single annular groove or raised ring discussed above in connection with FIG. 22, each of these single non-annular features causes a variation in a dielectric function along the surface of the metal film proximate to the aperture. Referring again to Eq. (3) above, and setting the index i equal to 1, according to the various embodiments discussed below a single non-annular feature proximate to an aperture positioned at a "resonant distance" $\alpha_o$ from the aperture facilitates a resonance condition for surface plasmon enhance generation of radiation.

Figure 23:
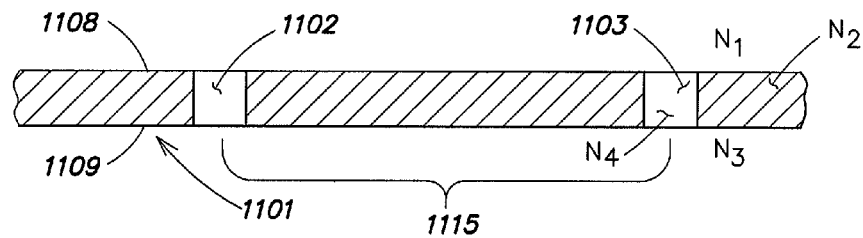
FIG. 23 is a cross-sectional view of a metal film in which a resonance configuration comprising two apertures is formed, according to one embodiment of the disclosure.

FIG. 23 is a cross-sectional view of a metal film 1101 in which a resonance configuration comprising two apertures is formed, according to one embodiment of the disclosure. In particular, the metal film 1101 has a first surface 1108 and a second surface 1109, and includes two apertures 1102 and 1103 extending between the first surface 1108 and the second surface 1109 and positioned adjacent to one another and separated by a resonant distance 1115 that constitutes the grating constant $a_o$ in Eq. (3) (with the index i equal to 1). In one aspect of this embodiment, apertures 1102 and 1103 essentially are the same size and have a diameter that is selected according to the needs of the particular application, with large apertures transmitting more light and creating larger illumination spot sizes. In exemplary implementations, apertures having a diameter on the order of 40-500 nm have been used in actual devices. It should be appreciated that in other implementations based on the concepts depicted in FIG. 23, one of the apertures 1102 may be substituted by a depression in the metal film that does not extend completely between the first surface 1108 and the second surface 1109, or a protrusion (protuberance) that extends outwardly from the first surface 1108 of the metal film.

As discussed above in connection with other embodiments, in yet another aspect the metal film 1101 of the embodiment of FIG. 23 is "optically thick" (e.g., having a thickness greater than two times the surface plasmon skin depth), so as to mitigate coupling of surface plasmons (coherent collective excitations of electrons) between the first surface 1108 of the metal film (the interface between media of respective refractive indices $N_1$ and $N_2$ that is irradiated with incident radiation) and the second surface 1109 of the film (the interface between media of respective refractive indices $N_3$ and $N_2$). In one exemplary implementation, the indices of refraction $N_1$, $N_3$, and $N_4$ are equal while $N_2$ (the index of refraction of the metal film 1101) is substantially different, wherein the metal film, unlike the surrounding material, is a conductor of electronic charges. Again, if the distance 1115 between the apertures 1102 and 1103 (or an aperture and a single other surface feature forming a resonance configuration), and the dielectric functions and thickness of the metal film, are tailored to attain a high transmission in accordance with Eq. (3) above (with i equal to 1), a significantly higher power density than that transmitted through a single aperture can be delivered through the two-element resonance configuration. This in turn allows a smaller hole size to be used, providing better resolution useful in numerous applications.

Figure 24:
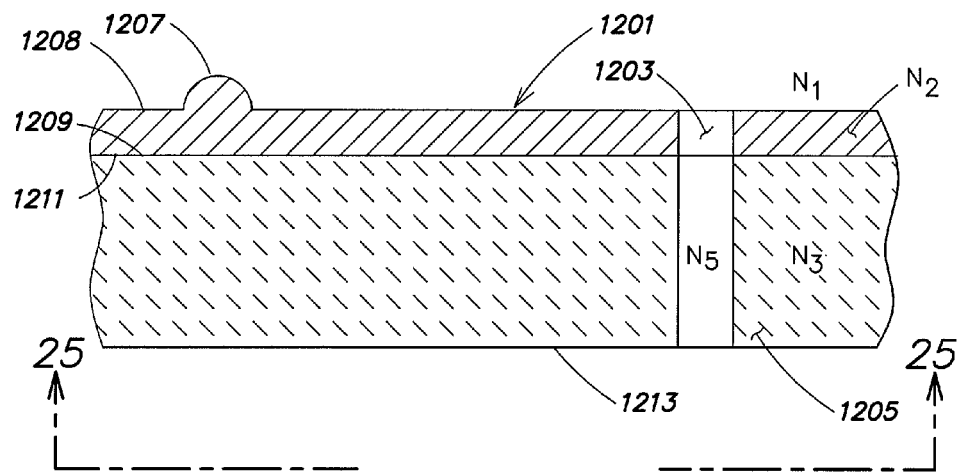
FIG. 24 is a cross-sectional view of a light barrier comprising a metal film on a dielectric substrate, in which a resonance configuration comprising one aperture and one protrusion (protuberance) extending upwardly from the metal film is formed, according to one embodiment of the disclosure.
Figure 25:
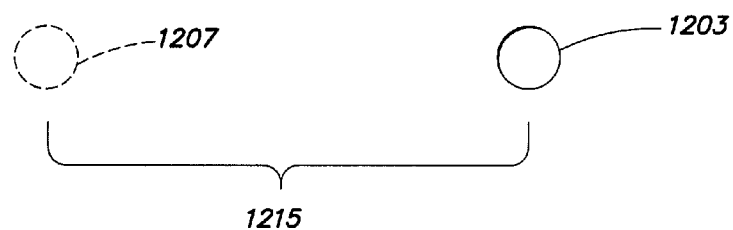
FIG. 25 is a bottom view of the light barrier of FIG. 24, taken along the line 25-25 indicated in FIG. 24.

FIG. 24 is a cross-sectional view of a light barrier structure comprising a metal film 1201 on a substrate 1205, in which a resonance configuration comprising one aperture 1203 and one protrusion (protuberance) 1207 extending upwardly from the metal film is formed, according to one embodiment of the disclosure. FIG. 25 is a bottom view of the light barrier of FIG. 24, taken along the line 25-25 indicated in FIG. 24. In FIG. 25, the protrusion 1207 is shown as a dashed line circle to the left of the solid line circle that indicates the aperture 1203, separated from each other by a resonant distance 1215. As with the embodiment shown in FIG. 23 above, it should be appreciated that in other implementations, the protrusion 1207 may be substituted by a depression in the metal film that does not extend completely through the metal film, or another aperture. With respect to a protrusion or a depression, in one aspect, a dimension of the protrusion or depression in a direction normal to the surface of the metal film may be on the order of (or greater than) a skin depth of surface plasmons induced by incident radiation that irradiates the metal film.

In the embodiment of FIGS. 24 and 25, as discussed above in connection with FIGS. 4-6, the substrate further serves to mitigate coupling of surface plasmons between a surface of the light barrier irradiated by incident radiation, and a surface of the light barrier from which surface plasmon enhanced radiation is generated. Accordingly, the generated surface plasmon enhanced radiation has an emission profile that is reduced relative to the embodiment of FIG. 23.

More specifically, as illustrated in FIG. 24, the metal film 1201 has a first surface 1208 that is irradiated by incident radiation (when present), and a second surface 1209 that is contiguous with a first substrate surface 1211 of the substrate 1205. The substrate 1205 also has a second substrate surface 1213 constituting a plane from which the surface plasmon enhanced radiation is emitted from the light barrier apparatus. In one aspect, the substrate is formed of a material that exhibits significant non-metallic behavior at frequencies corresponding to the incident radiation. For example, in various implementations, the substrate may be a dielectric material, or may alternatively be a metal (e.g., a "bad" metal as discussed above in connection with FIG. 20) having a significantly low conductivity at frequencies corresponding to the incident radiation.

In another aspect, the substrate 1205 in the embodiment illustrated in FIG. 24 may be formed of a material that is transparent to radiation at the frequency employed, such as quartz or glass. Although the aperture 1203 is depicted in FIG. 24 as extending through both the metal film 1201 and the substrate 1205, it should be appreciated that such a construction is not necessarily required in all cases. For example, in yet another aspect of this embodiment, if a transparent substrate is employed, the aperture 1203 need not extend completely through the substrate, which may facilitate ease of fabrication for some implementations.

Again, as discussed above in connection with FIGS. 4-6, the presence of the substrate 1205 in the embodiment of FIGS. 24 and 25 mitigates coupling of plasmons from the surface 1208 of the metal film 1201 to the surfaces 1211 and 1213 of the substrate 1205. This reduced coupling creates a smaller and more defined emission profile for the surface plasmon enhanced radiation generated by the apparatus. Other structures which also result in reduced emission profiles are discussed above in connection with FIGS. 13-20, and these structures also may be employed in any of the embodiments discussed herein in connection with non-periodic resonance configurations.

The use of a single feature adjacent to an aperture to form a resonance configuration in the embodiments depicted in FIGS. 23-25 provides a level of radiated flux (light power transmission) for the surface plasmon enhanced radiation generated by the apparatus that is comparable to the radiation generated by a resonance configuration including a periodic array of features. However, a simplified resonance configuration based on the concepts underlying FIGS. 23-25 results in an apparatus that generally is less sensitive to variations in the wavelength of the incident radiation or dimensional variations (i.e., the resonance condition corresponds to a generally wider bandwidth of incident radiation). Although the intensity of the radiation generated by an apparatus based on FIGS. 23-25 is reduced somewhat at the maximum wavelength corresponding to the resonance condition (as compared to apparatus having a periodic array of features), the wider bandwidth of the resonance condition compensates for the reduction in maximum wavelength intensity.

The use of a single feature adjacent to each hole also eliminates potential conflicts that can arise when the effective distance separating the aperture from plural features differs from feature to feature. Because of the inability to precisely position the different features during the fabrication process, as well as irregularities in the conductivity or smoothness of the intervening surface separating the aperture and different features, conflicting resonances can occur which adversely affect the overall performance and response of the apparatus. The use of a single feature together with a single aperture in a resonance configuration significantly mitigates these potential conflicts, and the generally broader wavelength response of the apparatus reduces its sensitivity to wavelength variations in the incident radiation.

Figure 26:
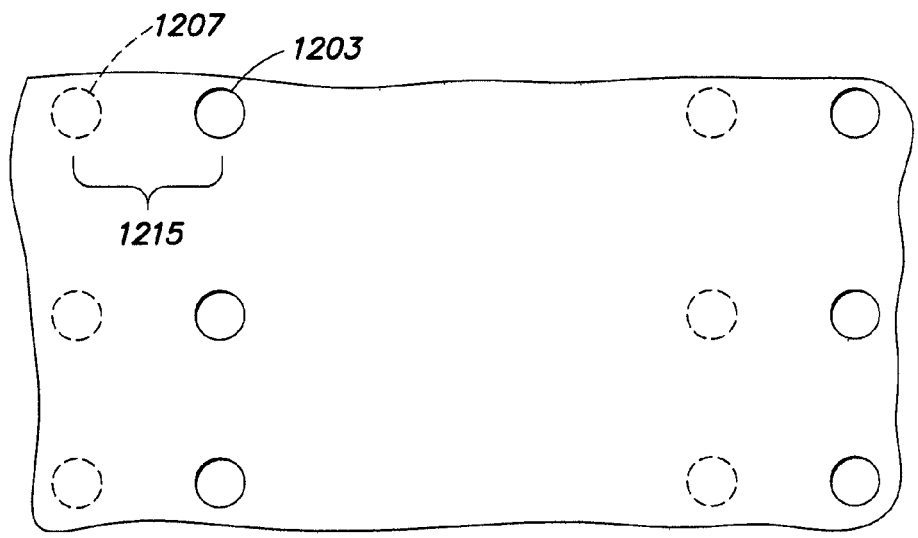
FIG. 26 is a plan view showing a layout of multiple resonance configurations formed in a metal film according to one embodiment of the disclosure, in which each resonance configuration of the layout is similar to the resonance configuration illustrated in FIGS. 24 and 25.

FIG. 26 is a plan view showing a layout of multiple resonance configurations formed in a metal film according to one embodiment of the disclosure, in which each resonance configuration of the layout is similar to the resonance configuration illustrated in FIGS. 24 and 25. The use of only a single additional feature with each light transmitting aperture may be used to advantage in applications, such as scanning optical microscopy, photolithography and data storage, where it is desired to employ a plurality of light sources operating in parallel. The plan view of FIG. 26 shows six apertures (one of which is depicted by the solid line circle 1203) and a nearby feature (another hole, a protrusion or a depression in the surface of the conductive film) depicted at 1207. The resulting structure is easier to fabricate, and each of the resonance configurations (i.e. each pair comprising an aperture and a single other feature) occupies a smaller footprint than would be the case if the aperture was positioned in a periodic array of features. While FIG. 26 illustrates six identical resonance configurations formed in a metal film, it should be appreciated that other embodiments according to the present disclosure are not limited in this respect. In particular, in other implementations, any two or more of multiple resonance configurations formed in a metal film may have a different structure (e.g., two apertures, an aperture and a depression, and aperture and a protrusion, etc.), and virtually any number of multiple resonance configurations may be formed in a metal film for a variety of applications.

For purposes of the present disclosure, in yet other embodiments, a "non-periodic structure" also refers to a resonance configuration that includes three or more elements (including an aperture) proximate to each other in a metal film, in which any two distances between adjacent elements is not equal, and/or a shape and/or dimension of any two elements is not equal. In various implementations of this embodiment, examples of one or more features in addition to a single aperture to form such a resonance configuration include, but are not limited to, one or more topographic features (protrusion(s), depression(s), groove(s), raised ring(s), etc.) having different shapes and/or dimensions from the aperture, as well as one or more edges of a metal film in which the aperture is formed. For example, an aperture may be defined in and through a metal film having an otherwise smooth surface (no significant topological features) that terminates at one or more edges spaced at a resonant distance from the aperture. Again, each of the foregoing features causes a variation in a dielectric function along the surface of the metal film proximate to the aperture.

Figure 27:
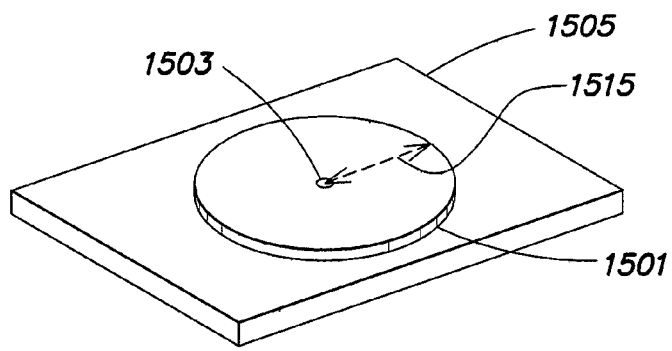
FIG. 27 is a perspective view of a disk-shaped metal film that forms a resonance configuration comprising a single aperture in the metal film, according to one embodiment of the disclosure.

FIG. 27 is a perspective view of a disk-shaped metal film that forms a resonance configuration having a non-periodic structure comprising a single aperture in the metal film, according to one embodiment of the disclosure. In FIG. 27, a central aperture 1503 passes through a metal film 1501 that is supported on a substrate 1505. A radius 1515 of the disk-shaped metal film is approximately equal to the grating constant $a_o$ given in Eq. (3) above (with the index i equal to 1). Alternatively, the implementation shown in FIG. 27 may be considered in some sense analogous to the resonance condition given in Eq. (4) above, in which the radius 1515 provides the parameter $\rho$. In one aspect of this embodiment, the surface of the disk-shaped metal film preferably is smooth and substantially free of surface irregularities. As in other embodiments discussed above, the substrate may be a dielectric material or another material exhibiting significantly non-metallic behavior at frequencies corresponding to the incident radiation (e.g., a "bad" metal). The single edge of the disk-shaped metal film creates a non-periodic structure with the aperture, not only because there are essentially only two features (i.e., aperture and edge) constituting the resonance configuration, but also because the effectively infinite width of the edge in cross-section is significantly different than a cross-sectional width of the aperture. Also, as discussed above in connection with other embodiments, a thickness of the metal film represented by the edge of the film generally is greater than a skin depth of surface plasmons induced by incident radiation that irradiates the metal film.

Figure 28:
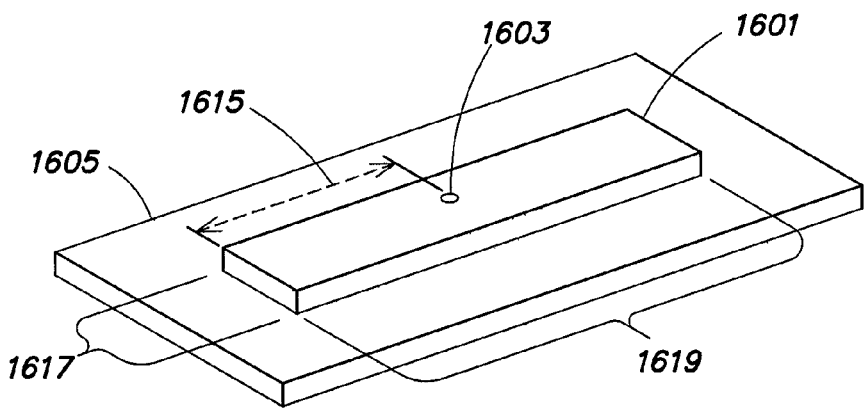
FIG. 28 is a perspective view of an elongate-shaped metal film that forms a resonance configuration comprising a single aperture in the metal film, according to one embodiment of the disclosure.

FIG. 28 is a perspective view of an elongate-shaped metal film that forms a non-periodic resonance configuration comprising a single aperture in the metal film, according to yet another embodiment of the disclosure. In FIG. 28, the aperture 1603 is defined in and extends through an elongate-shaped metal film 1601 having a short dimension 1617 and a long dimension 1619 orthogonal to the short dimension. In FIG. 28, the elongate shape of the film is in the form of a rectangular shape. In this particular example, the aperture 1603 is located equidistant from first and second opposing edges of the rectangular shape. In one aspect, the distance 1615 between the aperture and one of the edges of the long dimension provides the grating constant $a_o$ in Eq. (3) (alternatively, as discussed below, a resonance condition may be established based on a grating constant derived from a distance along the short dimension). As in the embodiments discussed above, the metal film may be coupled to a substrate 1605, and the substrate may be a dielectric material or another material exhibiting significantly non-metallic behavior at frequencies corresponding to the incident radiation (e.g., a "bad" metal).

Figure 29:
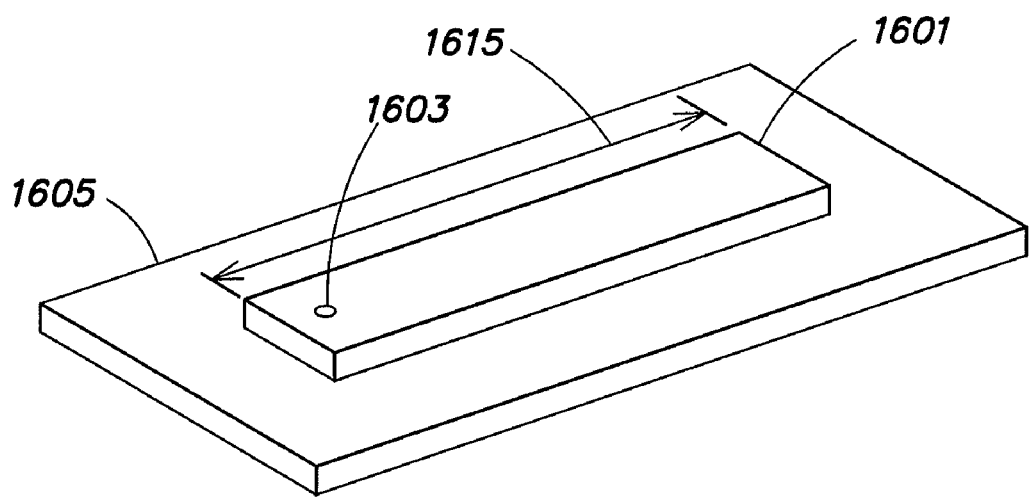
FIG. 29 is a perspective view of an elongate-shaped metal film that forms a resonance configuration comprising a single aperture located proximate to one end of the metal film, according to one embodiment of the disclosure.

In the apparatus illustrated in FIG. 28, the distance 1615 constitutes a resonance distance for incident radiation having an electric field polarization oriented parallel to the long dimension 1619 of the metal film 1601. Alternatively, a distance along the short dimension 1617 between the aperture and one edge may constitute the resonance distance for incident radiation polarized along the short dimension. In yet another alternative implementation shown in FIG. 29, to achieve an even smaller footprint for the resonance configuration, the aperture 1603 may be positioned at one end of an elongated structure whose overall length constitutes the resonance distance 1615 (i.e., is approximately equal to the grating constant $\alpha_o$).

Figure 30:
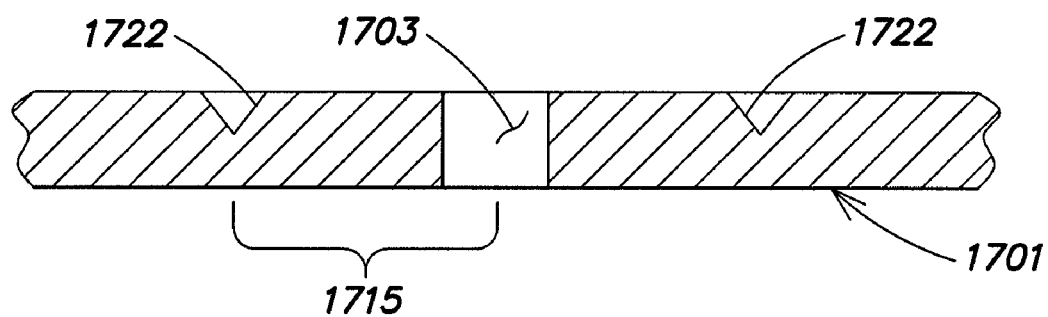
FIG. 30 is a cross-sectional view of a metal film in which is formed a non-periodic resonance configuration comprising an aperture and two additional features having different shapes/dimensions from the aperture, according to one embodiment of the disclosure.

FIG. 30 is a cross-sectional view of a metal film 1701 in which is formed another example of non-periodic resonance configuration according to one embodiment of the disclosure. In FIG. 20, the non-periodic resonance configuration comprises an aperture 1703 and two additional features 1722 having different shapes/dimensions from the aperture. In the embodiment of FIG. 30, although both of the features 1722 may be spaced a resonant distance 1715 from the aperture 1703, the resonance configuration nonetheless is non-periodic, due to the different cross-sectional profiles of at least two of the features forming the resonance configuration. As discussed above in connection with other embodiments, the metal film 1701 may be coupled to a substrate, and the substrate may be a dielectric material or another material exhibiting significantly non-metallic behavior at frequencies corresponding to the incident radiation (e.g., a "bad" metal).

In accordance with various aspects of the invention, means may be employed with any of the single aperture configurations discussed herein for limiting the extent of surface plasmon excitation at the exit surface of the emitting hole to the hole itself, or to a small area surrounding the rim of the hole at its exit, thereby confining the area of illumination to achieve higher resolution. All of the light barrier configurations described above in connection with FIGS. 4-20 may be employed to limit the illumination area produced by the emitting hole.

Having thus described illustrative embodiments, it is to be appreciated that various alterations, modifications, and improvements will readily occur to those skilled in the art. Such alterations, modifications, and improvements are intended to be part of this disclosure, and are intended to be within the spirit and scope of this disclosure. While some examples presented herein involve specific combinations of functions or structural elements, it should be understood that those functions and elements may be combined in other ways according to the present disclosure to accomplish the same or different objectives. In particular, acts, elements, and features discussed in connection with one embodiment are not intended to be excluded from similar or other roles in other embodiments. Accordingly, the foregoing description and attached drawings are by way of example only, and are not intended to be limiting.

The invention claimed is:

1. An apparatus, comprising:
a metal film having a first surface and a second surface; and
at least one resonance configuration formed in the metal film, the at least one resonance configuration comprising:
an aperture extending between the first surface and the second surface; and
at least one feature, not including another aperture, that forms a non-periodic structure together with the aperture, the at least one feature causing a variation in a dielectric function along the first surface proximate to the aperture,
wherein the aperture and the at least one feature are configured so as to cooperatively facilitate a resonance condition for surface plasmon enhanced radiation generated by the apparatus, based on incident radiation, when present, that irradiates the first surface of the metal film.

2. The apparatus of claim 1, wherein the at least one resonance configuration comprises a plurality of resonance configurations formed in the metal film.

3. The apparatus of claim 1, wherein the plurality of resonance configurations comprises a plurality of identical resonance configurations.

4. The apparatus of claim 1, wherein the at least one feature comprises a single feature.

5. The apparatus of claim 4, wherein the at least one resonance configuration comprises a plurality of resonance configurations formed in the metal film.

6. The apparatus of claim 5, wherein each resonance configuration of the plurality of resonance configurations comprises a single aperture and a single feature configured so as to cooperatively facilitate the resonance condition for the surface plasmon enhanced radiation.

7. The apparatus of claim 4, wherein the at least one feature comprises a single annular groove in the metal film, the single annular groove surrounding the aperture.

8. The apparatus of claim 7, wherein the aperture has a first diameter, and wherein a width of the single annular groove is equal to the first diameter.

9. The apparatus of claim 7, wherein a depth of the single annular groove in the metal film is greater than a skin depth of surface plasmons induced by the incident radiation.

10. The apparatus of claim 4, wherein the single feature comprises a single raised ring surrounding the aperture.

11. The apparatus of claim 10, wherein the aperture has a first diameter, and wherein a width of the single raised ring is equal to the first diameter.

12. The apparatus of claim 4, wherein the single feature comprises a protrusion that extends outwardly from the first surface of the metal film.

13. The apparatus of claim 4, wherein the single feature comprises a depression in the metal surface, wherein the depression does not completely extend between the first and second surfaces of the metal film.

14. The apparatus of claim 1, wherein the metal film has at least one edge, and wherein the at least one feature comprises the at least one edge of the metal film.

15. The apparatus of claim 14, wherein the metal film has a circular shape such that the at least one edge forms an annular edge around the aperture.

16. The apparatus of claim 14, wherein the metal film has a polygonal shape forming a plurality of edges including the at least one edge.

17. The apparatus of claim 14, wherein the metal film has an elongate shape.

18. The apparatus of claim 17, wherein the elongate shape has a short dimension and a long dimension orthogonal to the short dimension, wherein the long dimension has a first end and a second end, and wherein the aperture is disposed proximate to one of the first end and the second end.

19. The apparatus of claim 18, wherein the elongate shape is a rectangular shape.

20. The apparatus of claim 17, wherein the elongate shape is a rectangular shape, wherein the aperture is located equidistant from first and second opposing edges of the rectangular shape, and wherein at least one of the first and second opposing edges constitutes the at least one feature.

21. The apparatus of claim 1, further comprising a substrate having a first substrate surface substantially contiguous with the second surface of the metal film, the substrate further having a second substrate surface constituting a plane from which the surface plasmon enhanced radiation is emitted from the apparatus, wherein the substrate exhibits significant non-metallic behavior at frequencies corresponding to the incident radiation.

22. The apparatus of claim 21, wherein the at least one feature comprises a single feature.

23. The apparatus of claim 21, wherein the substrate comprises a dielectric material.

24. The apparatus of claim 21, wherein the substrate comprises a metallic material having a significantly low conductivity at the frequencies corresponding to the incident radiation.

25. The apparatus of claim 21, wherein the substrate is transparent with respect to the incident radiation.

26. The apparatus of claim 21, further comprising at least one second feature causing a variation in a second dielectric function along the second substrate surface of the substrate so as to reduce an emission profile of the surface plasmon enhanced radiation generated by the apparatus.

27. The apparatus of claim 26, wherein the aperture extends between the first substrate surface and the second substrate surface, and wherein the at least one second feature comprises an annular ring of conductive material proximate to the second substrate surface and surrounding the aperture.

28. The apparatus of claim 26, further comprising a second metal film substantially contiguous with the second substrate surface, wherein the aperture extends through the second metal film, and wherein the at least one second feature comprises a groove formed in the second metal film and surrounding the aperture.

29. An apparatus, comprising:
a metal film having a first surface and a second surface; and
at least one resonance configuration formed in the metal film, the at least one resonance configuration comprising:
an aperture extending between the first surface and the second surface; and
a single feature, not including another aperture, that causes a variation in a dielectric function along the first surface proximate to the aperture,
wherein the aperture and the single feature are configured so as to cooperatively facilitate a resonance condition for surface plasmon enhanced radiation generated by the apparatus, based on incident radiation, when present, that irradiates the first surface of the metal film.

30. The apparatus of claim 29, wherein the single feature comprises a single topographic feature.

31. The apparatus of claim 30, wherein the single topographic feature comprises a single annular groove in the metal film, the single annular groove surrounding the aperture.

32. The apparatus of claim 30, wherein the single topographic feature comprises a single raised ring surrounding the aperture.

33. The apparatus of claim 30, wherein the single topographic feature comprises a second aperture.

34. The apparatus of claim 30, wherein the single topographic feature comprises a protrusion that extends outwardly from the first surface of the metal film.

35. The apparatus of claim 30, wherein the single topographic feature comprises a depression in the metal surface, wherein the depression does not completely extend between the first and second surfaces of the metal film.

36. The apparatus of claim 29, further comprising a substrate having a first substrate surface substantially contiguous with the second surface of the metal film, the substrate further having a second substrate surface constituting a plane from which the surface plasmon enhanced radiation is emitted from the apparatus, wherein the substrate exhibits significant non-metallic behavior at frequencies corresponding to the incident radiation.

37. The apparatus of claim 36, wherein the substrate comprises a dielectric material.

38. The apparatus of claim 36, wherein the substrate comprises a metal having a significantly low conductivity at frequencies corresponding to the incident radiation.

39. The apparatus of claim 36, wherein the substrate is transparent with respect to the incident radiation.

40. The apparatus of claim 36, further comprising at least one second feature causing a variation in a second dielectric function along the second substrate surface of the substrate so as to reduce an emission profile of the surface plasmon enhanced radiation generated by the apparatus.

41. The apparatus of claim 40, wherein the aperture extends between the first substrate surface and the second substrate surface, and wherein the at least one second feature comprises an annular ring of conductive material proximate to the second substrate surface and surrounding the aperture.

42. The apparatus of claim 40, further comprising a second metal film substantially contiguous with the second substrate surface, wherein the aperture extends through the second metal film, and wherein the at least one second feature comprises a groove formed in the second metal film and surrounding the aperture.

* * * * *